United States Patent [19]

Forman et al.

[11] Patent Number: 5,505,699
[45] Date of Patent: Apr. 9, 1996

[54] ANGIOPLASTY DEVICE

[75] Inventors: Michael R. Forman, St. Paul; Michael N. Helmus, St. Louis Park; Joseph E. Laptewicz, Jr., Eden Prairie, all of Minn.

[73] Assignee: Schneider (USA) Inc., Plymouth, Minn.

[21] Appl. No.: 217,306

[22] Filed: Mar. 24, 1994

[51] Int. Cl.$^6$ ................................................ A61M 29/00
[52] U.S. Cl. ............................ 604/96; 604/280; 128/772; 128/898; 606/198
[58] Field of Search ................................ 604/96–102, 264, 604/280; 128/656–658, 772; 606/191, 192, 194, 198

[56] References Cited

U.S. PATENT DOCUMENTS

| | | |
|---|---|---|
| Re. 33,166 | 2/1990 | Samson . |
| 4,800,890 | 1/1989 | Cramer . |
| 4,838,268 | 6/1989 | Keith et al. . |
| 4,846,174 | 7/1989 | Willard et al. . |
| 4,873,983 | 10/1989 | Winters .................... 128/772 |
| 4,883,459 | 11/1989 | Calderon .................. 128/656 |
| 4,917,088 | 4/1990 | Crittenden . |
| 4,925,445 | 5/1990 | Sakamoto et al. . |
| 4,946,466 | 8/1990 | Pinchuk et al. . |
| 4,984,581 | 1/1991 | Stice . |
| 5,102,390 | 4/1992 | Crittenden et al. . |
| 5,104,376 | 4/1992 | Crittenden . |
| 5,120,308 | 6/1992 | Hess . |
| 5,167,239 | 12/1992 | Cohen .................... 128/772 |
| 5,180,367 | 1/1993 | Kontos .................... 604/101 |
| 5,209,727 | 5/1993 | Radisch, Jr. et al. . |
| 5,211,183 | 5/1993 | Wilson . |
| 5,238,004 | 8/1993 | Sahatjian et al. . |
| 5,242,394 | 9/1993 | Tremulis .................. 604/96 |
| 5,242,451 | 9/1993 | Marada et al. ........... 606/198 |
| 5,243,996 | 9/1993 | Hall . |
| 5,265,622 | 11/1993 | Barbere .................. 128/772 |
| 5,277,199 | 1/1994 | DuBois .................. 128/657 |
| 5,281,200 | 1/1994 | Corso, Jr. et al. . |
| 5,313,967 | 5/1994 | Lieber .................... 128/772 |
| 5,344,425 | 9/1994 | Sawyer .................. 606/198 |

FOREIGN PATENT DOCUMENTS

| | | |
|---|---|---|
| 0491349 | 6/1992 | European Pat. Off. . |
| 0515201 | 11/1992 | European Pat. Off. . |
| 8908472 | 9/1989 | WIPO . |
| 9013329 | 11/1990 | WIPO . |
| 9323107 | 11/1993 | WIPO . |

*Primary Examiner*—C. Fred Rosenbaum
*Assistant Examiner*—Chris Smith
*Attorney, Agent, or Firm*—Peter C. Richardson; Lawrence C. Akers; Philip C. Strassburger

[57] ABSTRACT

This invention relates to an angioplasty device that is formed from a hollow metallic tube, a balloon affixed adjacent the distal end of the tube and being in fluid communication with the lumen of the tube, a flexible distal segment connected to the distal end of the tube and a removable hub connected adjacent to the proximal end of the tube. The tube is preferably formed from a superelastic material such as nickel-titanium alloy. This invention also relates to various methods of using this angioplasty device.

24 Claims, 5 Drawing Sheets

ANGIOPLASTY DEVICE

BACKGROUND OF THE INVENTION

The present invention relates to an angioplasty device which can take the form of a hollow metallic guide wire with a balloon mounted on the distal end thereof.

Balloon angioplasty is an effective method for treating vascular disease, especially atherosclerosis. The build up of plaque in the lumen of a blood vessel, i.e. a stenosis, narrows the lumen and may possibly totally occlude the lumen if left untreated. Such a situation in a coronary artery is known as a myocardial infarction, i.e. a heart attack.

Prior to the advent of balloon angioplasty, the treatment for a stenotic lesion in a blood vessel was bypass surgery. This required an artificial graft or one of the patient's other blood vessels to be used to bypass the diseased vessel. In order to properly position the replacement blood vessel, major surgery was required to give the physician access to the body site to be treated so the replacement blood vessel could be sewn in place.

In balloon angioplasty, a balloon located on the distal end of a catheter is used to expand the blood vessel to restore its patency in the area of the stenotic lesion. The existence and location of a stenotic lesion is first determined by using a diagnostic catheter to inject contrast fluid to the affected area which is viewed under fluoroscopy.

Where a coronary artery is to be treated, i.e., in a PTCA (percutaneous transluminal coronary angioplasty) procedure, the balloon dilatation catheter typically enters the body at an access site, typically at the femoral artery, remote from the blood vessel to be treated and is maneuvered in the vascular system to the treatment site. Before a balloon dilatation catheter can be maneuvered into place, a guide catheter, with a J wire disposed therein and extending beyond the distal end, is typically inserted into the femoral artery in the groin area and maneuvered through the vasculature, around the aortic arch, where the J wire is removed, to the appropriate coronary ostium for the coronary artery to be treated. The guide catheter provides backup support for advancement of the balloon dilatation catheter to the treatment site. The guide catheter also allows adequate amounts of contrast fluid to be injected therethrough with the balloon dilatation catheter therein so the physician can visualize the treatment site under fluoroscopy during the procedure.

Where a wire guided balloon dilatation catheter, i.e. an over the wire balloon dilatation catheter or a rapid exchange balloon dilatation catheter, is to be used, a metallic guide wire will be guided through the guide catheter to the treatment site first to provide a path over which the balloon dilatation catheter can travel. The guide wire is inserted in the guide catheter so it extends past the distal end of the guide catheter and across the stenotic lesion to be treated. This provides the balloon dilatation catheter with access to the stenotic lesion to be treated.

Where a fixed wire balloon dilatation catheter is used, no separate guide wire is needed. Instead the balloon dilatation catheter has a wire fixed to it that serves to guide the balloon dilatation catheter to the treatment site.

One problem that may occur is when the stenosis substantially occludes the lumen of the blood vessel. If the profile (outer diameter) of the balloon dilatation catheter is too large, it will be unable to cross the lesion to allow the balloon to inflate and restore patency to the blood vessel. A related problem occurs when the stenosis is located in a very narrow blood vessel. These lesions may be inaccessible to a standard balloon dilatation catheter, which has a typical outer diameter of about 0.032 to about 0.036 inches (about 0.081 cm to about 0.091 cm) along its distal portion. Although guide wires which have an outer diameter of 0.014 inches to 0.018 inches (0.036 cm to 0.046 cm) may be able to cross a very tight stenosis in an extremely narrow blood vessel, such guide wires can not dilate the stenosis.

Another problem may occur in a balloon angioplasty procedure where the physician may have to use more than one balloon dilatation catheter, i.e. exchange balloon dilatation catheters, if the balloon on the original balloon dilatation catheter is not of the proper size to safely and fully treat the stenotic lesion. This is not a major problem for wire guided balloon dilatation catheters because the guide wire can remain in place across the stenosis while the balloon dilatation catheters are exchanged. On the other hand, if a fixed wire balloon dilatation catheter is used, access to the stenotic lesion will be lost if that catheter is removed.

After the angioplasty procedure, a stent may be used to support the vessel wall. These stents are used to enlarge and support the lumen, provide a smooth luminal surface, reinforce vessel dissections, tack-up tissue flaps, reduce the risk of plaque rupture, decrease the incidence of complications and reduce the incidence of restenosis. Many different types of stents may be used, such as radially self-expanding stents or balloon-expandable stents. Typically, the stent is placed on the distal end of a wire guided delivery catheter so the stent can be maneuvered adjacent to the treatment site and deployed there. After deployment it may be necessary in certain circumstances to expand the stent further after it has been deployed. This requires the use of an additional balloon catheter that must be maneuvered to the stent so the balloon can expand the stent further. Because of all of the steps and the different devices necessary to perform this procedure, the risk of trauma to the patient is high.

It is therefore an object of the invention to provide an angioplasty device that can cross a very tight stenosis or cross an extremely narrow blood vessel and dilate a stenotic lesion.

It is a further object of this invention to provide an angioplasty device that acts as a guide wire that can predilate a stenosis.

It is still a further object of this invention to provide an angioplasty device that can be used with typical angioplasty balloon dilatation catheters where a balloon exchange is indicated.

It is yet another object of the invention to provide an angioplasty device that minimizes the number of different interventional devices needed to perform balloon angioplasty and further expand a stent at the site of the angioplasty procedure.

SUMMARY OF THE INVENTION

These and other objects are achieved by the angioplasty device of this invention. This angioplasty device is comprised of a hollow metallic tube, a balloon affixed adjacent the distal end of the metallic tube in fluid communication therewith, a flexible distal segment connected to the distal end of the metallic tube and a removable hub connected adjacent the proximal end of the metallic tube. In order for the angioplasty device to be able to be maneuvered to a treatment site in a coronary artery, it must be both flexible and stiff. Preferably the metallic tube is made from a shape-memory or superelastic material. Such a material includes nickel-titanium alloys, nickel and its alloys and titanium and its alloys. This material allows the angioplasty device to be formed with an outer diameter as small as about 0.010 inches (0.025 cm) so it can function as a standard guide wire for a PTCA balloon dilatation catheter or a stent delivery catheter when the hub is removed from its proximal end.

DETAILED DESCRIPTION OF THE INVENTION

Figure 1:
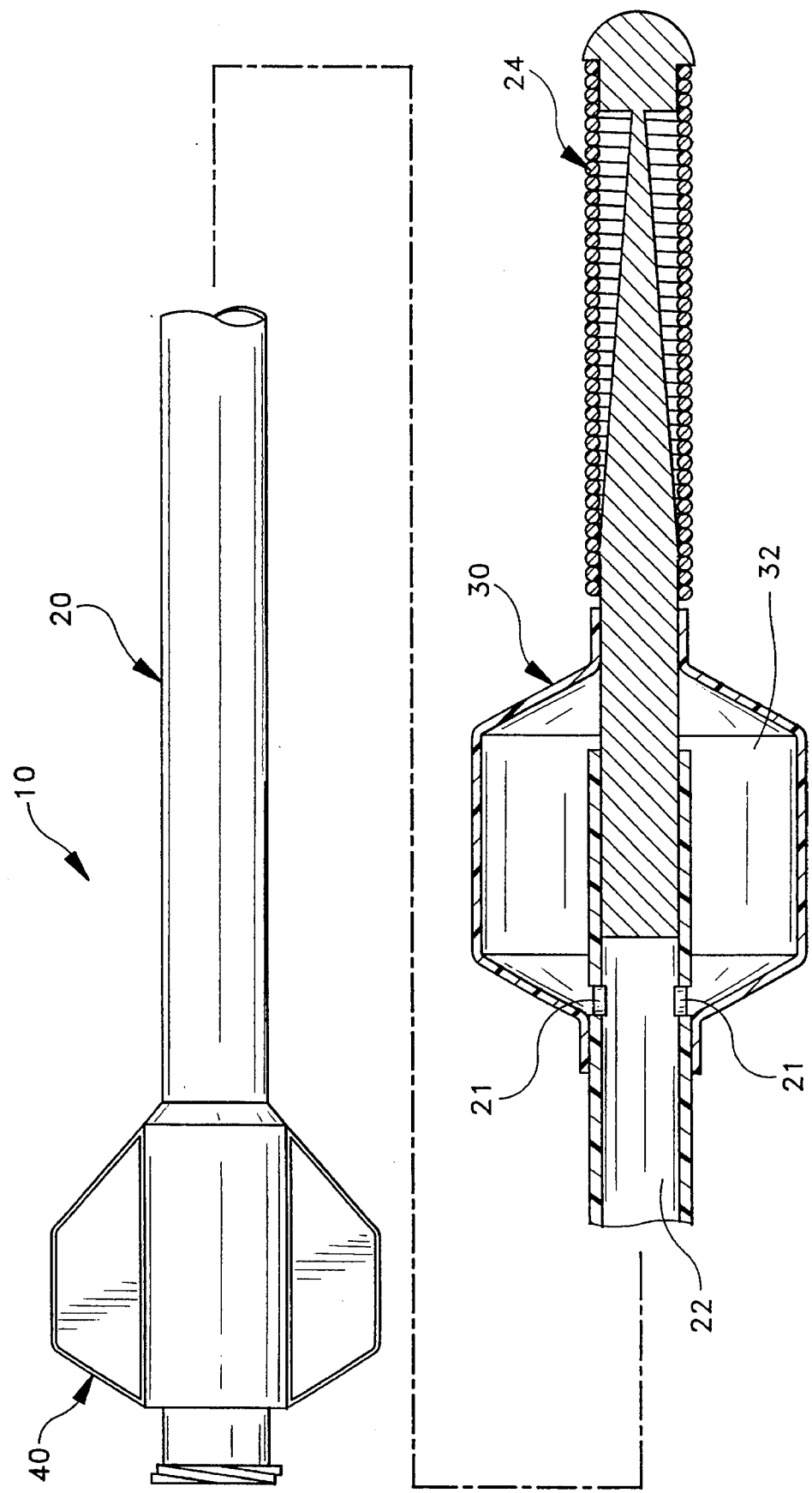
FIG. 1 is a side elevational view partially in section of one embodiment of the angioplasty device of this invention.

The angioplasty device 10 of this invention includes a hollow metallic tube 20. Preferably tube 20 has an outer diameter of less than about 0.06 inches (0.15 cm) and preferably is about 0.014 inches (0.036 cm). This dimension allows device 20 to be inserted into very small blood vessels and allows it to cross very tight lesions. In addition, standard coronary guide wires have an outer diameter of 0.014 inches (0.036 cm). Thus by making the outer diameter of the hollow metallic tube 20 this dimension, i.e. 0.014 inches (0.036 cm), device 20 may serve as a guide wire for standard balloon dilatation catheters used in the coronary arteries. It is to be understood that larger dimensions may be used if device 20 is not to be used as a guidewire for other balloon dilatation catheters. The wall thickness of tube 20 can vary between about 0.004 inches (0.01 cm) and about 0.002 inches (0.005 cm). The wall thickness should be large enough to maintain the structural integrity of tube 20 without unduly narrowing the lumen 22 of tube 20. Lumen 22 should remain large enough to allow balloon 30 to be inflated and deflated in a reasonable amount of time such as about 15 to 20 seconds.

In order for tube 20 to have lumen 22 extending therethrough yet have an outer diameter of about 0.014 inches, it should be formed from a shape-memory or superelastic material. Such a shape-memory or superelastic material is defined as an alloy that can be subjected to an apparent plastic deformation yet still return to its original shape when the load is released or when heated. This difference depends on the forming process of the shape-memory or superelastic material. It is to be understood that reference to a superelastic material hereinafter means a material having the above characteristics.

Suitable superelastic materials include nickel-titanium alloys (nitinol), nickel and its alloys or titanium and its alloys. Other examples of superelastic materials include, e.g., Silver-Cadmium (Ag—Cd), Gold-Cadmium (Au—Cd), Gold-Copper-Zinc (Au—Cu—Zn), Copper-Aluminum-Nickel (Cu—Al—Ni), Copper-Gold-Zinc (Cu—Au—Zn), Copper-Zinc (Cu—Zn), Copper-Zinc-aluminum (Cu—Zn—Al), Copper-Zinc-Tin (Cu—Zn—Sn), Copper-Zinc-Xenon (Cu—Zn—Xe), Iron Beryllium ($Fe_3Be$), Iron Platinum ($Fe_3Pt$), Indium-Thallium (In—Tl), iron-manganese (Fe—Mn), Nickel-Titanium-Vanadium (Ni—TiV), Iron-Nickel-Titanium-Cobalt (Fe—Ni—Ti—Co) and Copper-Tin (Cu—Sn). See Schetsky, L. McDonald, "Shape Memory Alloys", *Encyclopedia of Chemical Technology* (3rd ed.), John Wiley & Sons, 1982, vol. 20. pp. 726–736 for a full discussion of superelastic alloys. One preferred nickel-titanium alloy can be obtained from Raychem Corporation of Menlo Park, Calif. under the trademark Tinel®. This material exhibits both flexibility and stiffness. In addition, this material is tough, strong, biocompatible and bondable to the other components of device 10.

A flexible distal segment 24 is connected to the distal end of tube 20. In the embodiment shown in FIG. 1, distal segment 24 includes a solid wire surrounded at least along its distal portion by a helical coil. In this embodiment, distal segment 24 closes lumen 22 of tube 20. A side port 21 located in the side wall of tube 20 places the balloon cavity 32 in fluid communication with lumen 22. The solid wire and helical coil could be formed from stainless steel. Alternatively, the solid wire could be formed from a superelastic material and the helical coil could be formed from tungsten.

Figure 2:
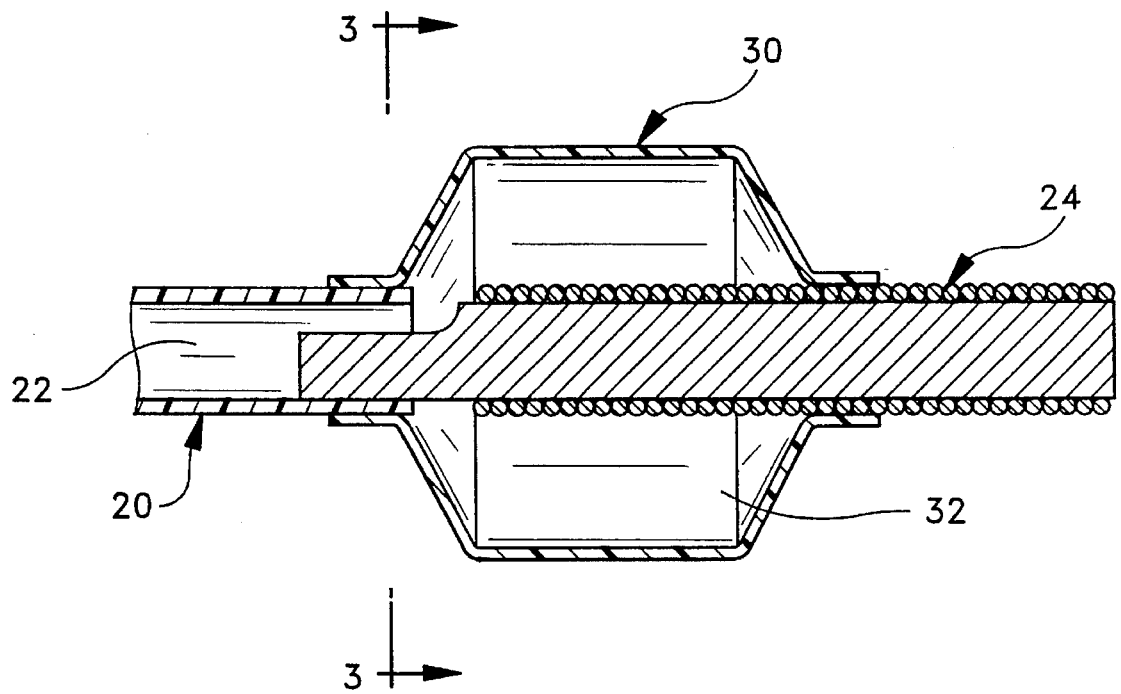
FIG. 2 is a side elevational view in section of the distal portion of another embodiment of the angioplasty device of this invention.
Figure 3:
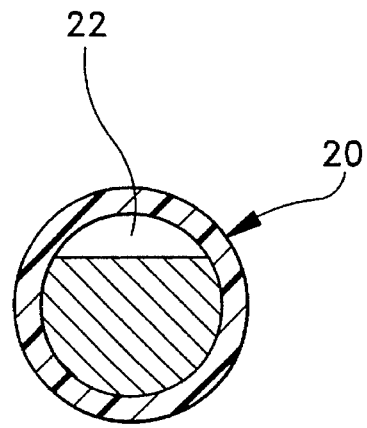
FIG. 3 is a cross-sectional view taken along line 3—3 in FIG. 2.
Figure 4:
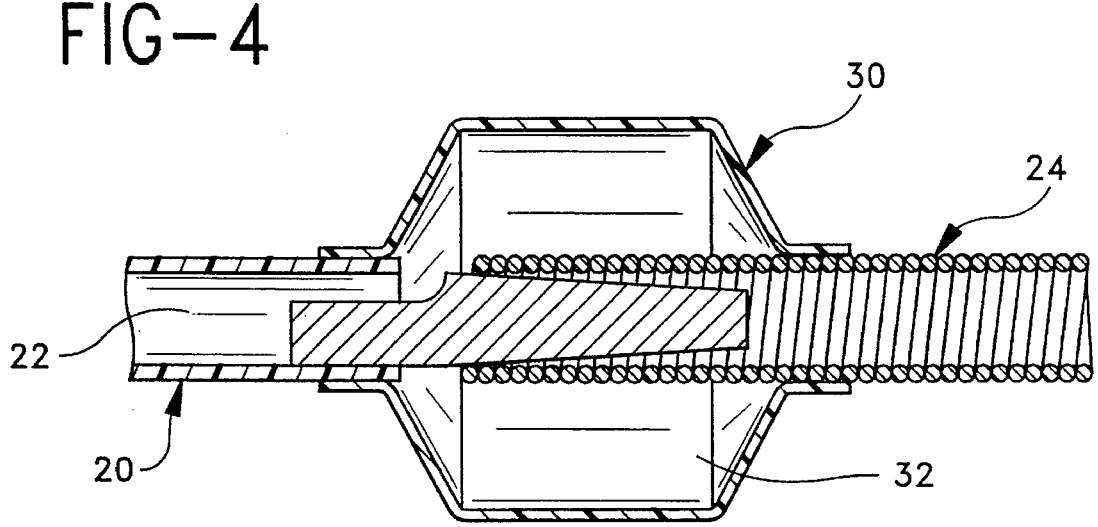
FIG. 4 is a side elevational view in section of the distal portion of yet another embodiment of the angioplasty device of this invention.
Figure 5:
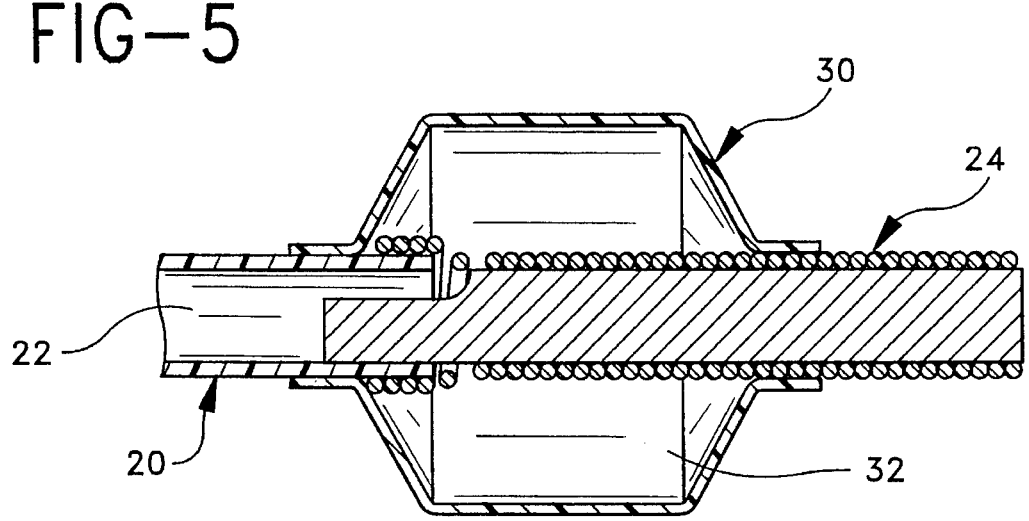
FIG. 5 is a side elevational view in section of the distal portion of yet another embodiment of the angioplasty device of this invention.

In a second embodiment, see FIG. 2, distal segment 24 does not close lumen 22 of tube 20. Instead the solid wire has a proximal portion affixed to the distal end of tube 20. The proximal portion of the solid wire does not fully plug lumen 22. This allows inflation fluid to flow out of the distal end of tube 20 into balloon cavity 32 which encompasses the distal end of tube 20. A helical coil is connected to the distal end of the solid wire. In this embodiment, the proximal neck of balloon 30 is affixed adjacent to the distal end of tube 20 while the distal neck of balloon 30 is connected to the helical coil. The solid wire of distal segment 24 may be tapered along its distal portion to increase its flexibility. See FIG. 4. Moreover, the solid wire may or may not extend to the distal end of the helical coil depending on the characteristics desired for distal segment 24. See FIG. 5.

Figure 6:
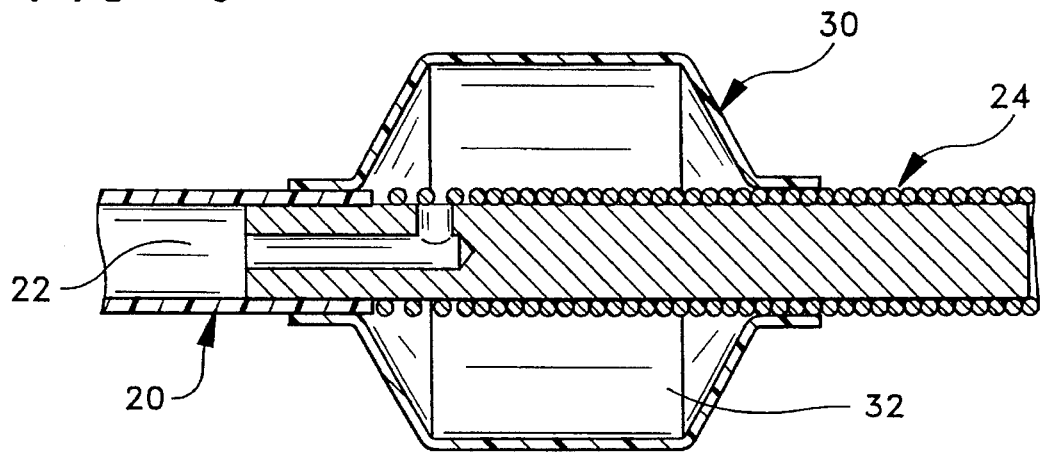
FIG. 6 is a side elevational view in section of the distal portion of yet another embodiment of the angioplasty device of this invention.

In yet another embodiment, see FIG. 6, the outer diameter of the solid wire of distal segment 24 is constant and is substantially equal to the inner diameter of the distal portion of tube 20. A small lumen is formed along a portion of the solid wire to provide a flow path to the balloon cavity for inflation fluid. Again, the distal end of the solid wire in this embodiment may or may not be tapered and may or may not extend to the distal end of the helical coil.

Balloon 30 can be formed from any suitable material such as polyethyleneterephthalate (PET), polyolefin, e.g. polyethylene or polyolefin copolymer (POC), polyamide, e.g. nylon, or polyurethane. Balloon 30 can be bonded to tube 20 and the helical coil by any standard bonding technique such as chemical adhesive or brazing.

The proximal end of device 10 includes a removable hub 40 to allow the attachment of other devices, such as an inflation/deflation device (not shown) to device 10. A standard Touhy Borst hub is preferably used.

Figure 7:
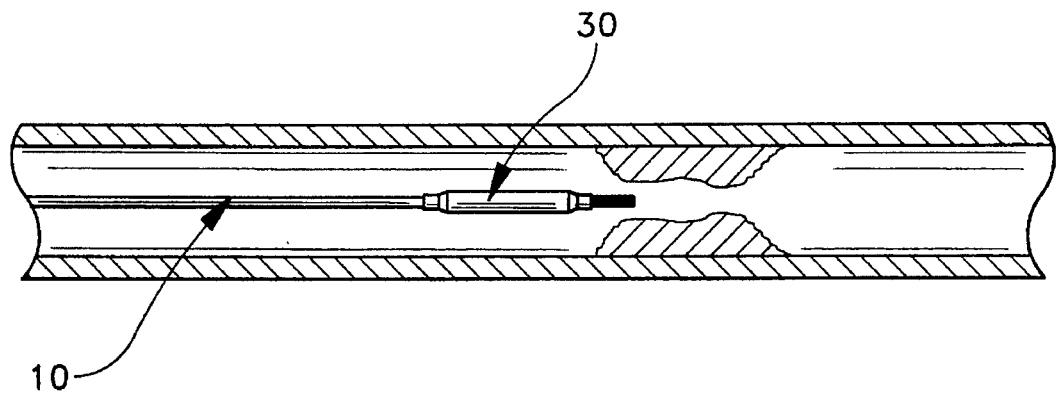
FIGS. 7–9 are schematic views showing a method of using the angioplasty device of this invention in a PTCA procedure.
Figure 8:
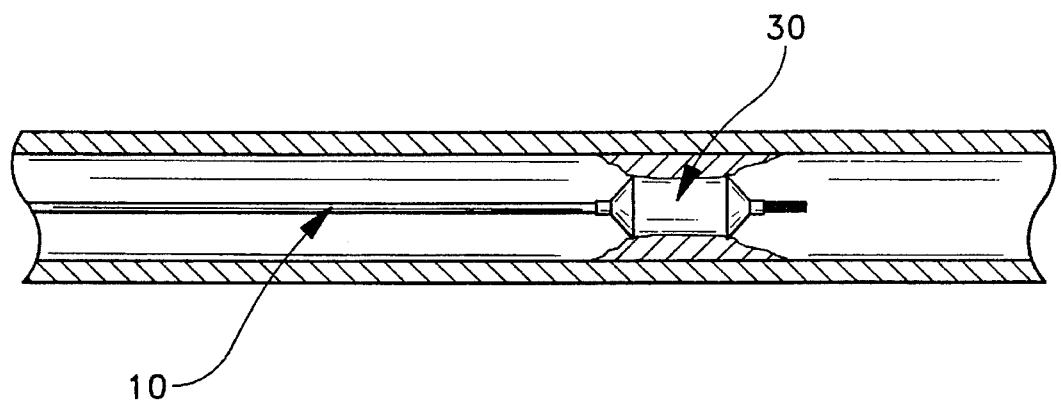
Figure 9:
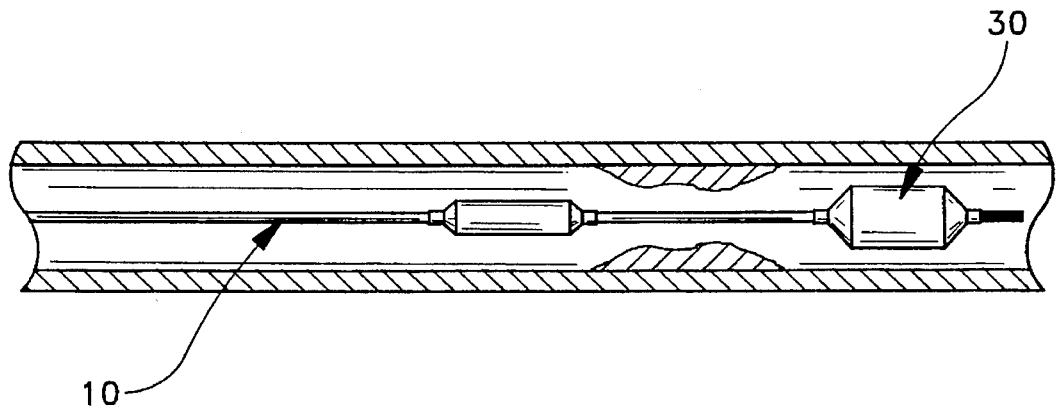

Device 10 can thus be used as a guide wire when hub 40 is removed. For example, once the guide catheter has been maneuvered into position, device 10 can be maneuvered through the guide catheter to the site of the stenosis just like a standard coronary guide wire. See FIG. 7. Then when balloon 30 is properly aligned at the stenosis, balloon 30 can be inflated to dilate the stenosis. See FIG. 8. Device 10 can be used either to "predilate" or fully dilate the stenosis. In either case, if a larger balloon is needed to fully dilate the stenosis, balloon 30 can be moved distally past the stenosis. Preferably balloon 30 is first deflated to facilitate movement of device 10 distally. Hub 40 is then removed and another wire guided balloon dilatation catheter with a different size balloon can be advanced over device 10 until the balloon of that catheter is located at the stenosis. The larger balloon can then fully dilate the stenosis. See FIG. 9. Once the procedure is complete both device 10 and the other balloon dilatation catheter can be removed.

Figure 10:
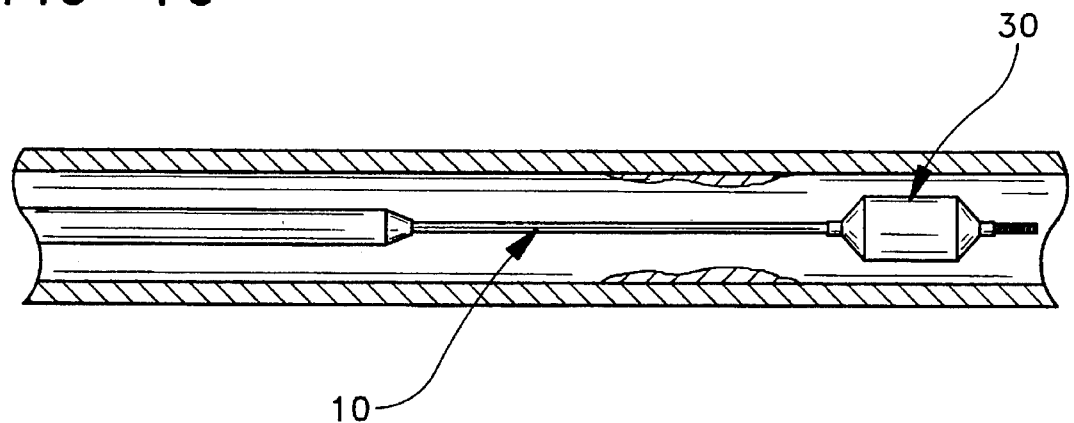
FIGS. 10–12 are schematic views showing a method of using the angioplasty device of this invention in a stent deployment procedure.
Figure 11:
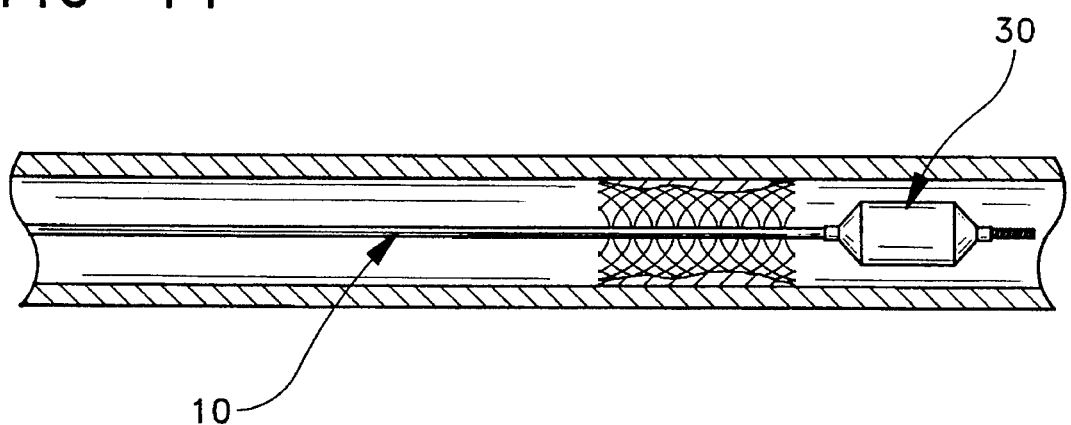
Figure 12:
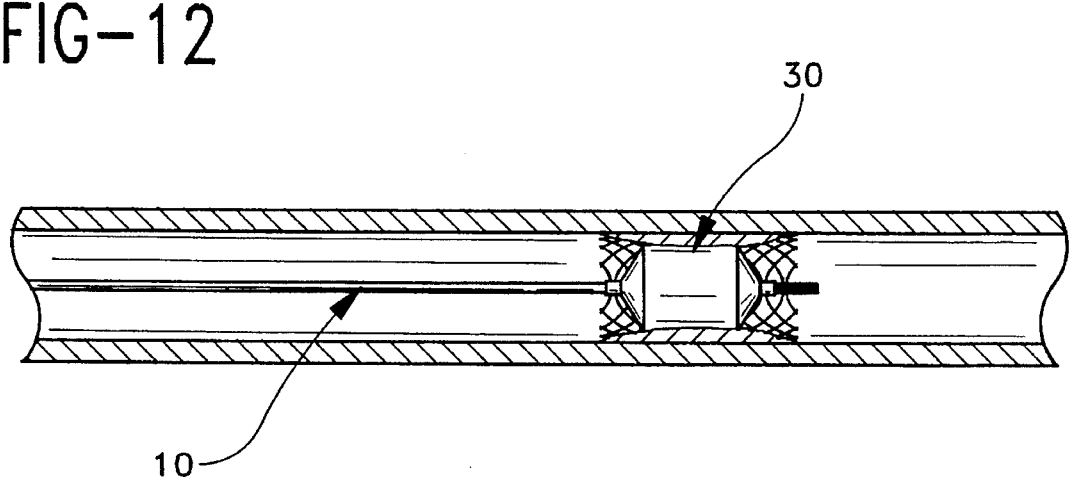

Furthermore, device 10 can also be used to further dilate a stent that has been deployed at the site of the lesion. After a PTCA procedure has been performed as outlined above, but before device 10 is withdrawn, a wire guided stent delivery catheter can be advanced over device 10 until the stent is properly aligned at the treatment site. See FIGS. 10 and 11. At this point the stent can be deployed in a conventional manner from the stent delivery catheter. If further expansion of the stent is desired, device 10 can be moved proximally inside of the stent. Balloon 30 is then inflated to further expand the stent. See FIG. 12. Balloon 30 is subsequently deflated and device 10 is removed.

Another advantage of device 10 is that it allows a physician to perform angiography, i.e. diagnostic procedures, and balloon angioplasty contemporaneously. In the typical situation, a patient suffering from what may be coronary artery disease will first undergo diagnostic tests to determine if the patient is a candidate for a PTCA procedure. Typically, a diagnostic catheter is inserted in a peripheral artery and maneuvered to the appropriate coronary artery. Then diagnostic fluid is injected through the diagnostic catheter to allow the physician to view the coronary arteries under fluoroscopy. If a PTCA procedure is indicated, the diagnostic catheter would be removed and a guide catheter would be maneuvered into position to begin a PTCA procedure. Alternatively, the patient would come back later for the PTCA procedure.

This scenario is not completely desirable because it subjects the patient to the risk of added trauma when the diagnostic catheter is removed and a guide catheter is inserted. However, this has been necessary because diagnostic catheters are generally inappropriate for use as a guide catheter for balloon dilatation catheters or guide wires because typical diagnostic catheters do not have a large enough lumen to allow both a standard balloon dilatation catheter and sufficient contrast fluid to pass therethrough. Typically, diagnostic catheters have a smaller lumen than a comparable guide catheter because the diagnostic catheter must have a thicker wall to withstand the pressure when contrast fluid is injected therethrough. For example, a 5 Fr. diagnostic catheter may have a lumen with an internal diameter of 0.042 inches (0.11 cm), a 6 Fr. diagnostic catheter may have a lumen with an internal diameter of 0.048 inches (0.12 cm) and a 7 Fr. diagnostic catheter may have a lumen with an internal diameter of 0.056 inches (0.14 cm). In comparison, for guide catheters the lumen diameter would be 0.063 inches (0.16 cm) in a 7 Fr. guide catheter.

With device 10 of this invention, a PTCA procedure can be done contemporaneously with the diagnostic procedure. After the diagnostic procedure confirms the need for the PTCA procedure, device 10 can be inserted through the diagnostic catheter and maneuvered to the lesion to be treated. The small shaft size of device 10 allows sufficient contrast fluid to be injected through the diagnostic catheter with device 10 still disposed therein to allow adequate visualization by the physician of the affected area under fluoroscopy. Moreover, the small size of device 10 facilitates its movement through the lumen of the diagnostic catheter. Once device 10 is properly positioned, balloon 30 can be inflated to dilate the lesion.

Although this invention has been described in connection with performing angioplasty and stent deployment procedures on coronary arteries, it is to be understood that the invention has equal applicability to angioplasty and stent deployment procedures performed in other peripheral arteries such as the carotid artery, renal artery and can be built to be compatible with 0.021 inch to 0.035 inch (0.053 cm to 0.089 cm) and/or 0.038 inch (0.097 cm) systems used in the periphery.

Thus it is seen that an angioplasty device is provided that can cross a very tight stenosis or an extremely narrow blood vessel, that acts as a guide wire to predilate or fully dilate a stenosis yet allows for the use of a typical angioplasty balloon dilatation catheter or stent delivery catheter thereover and that can be used to further expand the stent after deployment. One skilled in the art will appreciate that the described embodiments are presented for purposes of illustration and not of limitation and the present invention is only limited by the claims which follow.

We claim:

1. An angioplasty device having a proximal portion and a distal portion, the angioplasty device comprising:

(a) a hollow tube formed from a superelastic material and having a proximal portion and a distal portion and defining a lumen therein;

(b) a distal segment connected to the distal portion of the hollow tube, the distal segment having a longitudinal length and being solid along most of its longitudinal length with a fluid flow lumen in the distal segment in fluid communication with the hollow tube; and (c) a balloon defining a balloon cavity therein affixed to the distal portion of the angioplasty device and in fluid communication with the fluid flow lumen of the distal segment.

2. The angioplasty device of claim 1, wherein the distal portion of the hollow tube has an inside diameter and the distal segment has a proximal portion having an outside diameter slightly smaller than the inside diameter at the hollow tube, wherein the distal portion of the hollow tube is adapted to receive the proximal portion of the distal segment.

3. The angioplasty device of claim 2 wherein the fluid flow lumen of the distal segment has a diameter which is substantially smaller than the outside diameter of the proximal portion of the distal segment.

4. The angioplasty device of claim 1 further comprising a detachable hub connected to the proximal portion of the hollow tube.

5. The angioplasty device of claim 1 further comprising a helical coil spring arranged coaxially about the distal segment.

6. The angioplasty device of claim 1 wherein the superelastic material forming the hollow tube is selected from the group consisting of a nickel-titanium alloy, nickel and its alloys, and titanium and its alloys.

7. The angioplasty device of claim 1 wherein the distal segment comprises a superelastic material or stainless steel.

8. The angioplasty device of claim 1 wherein the distal segment has an outside diameter which remains essentially constant throughout its longitudinal length.

9. The angioplasty device of claim 1 wherein the distal segment tapers distally along at least part of its longitudinal length.

10. An angioplasty device having a proximal portion and a distal portion, the angioplasty device comprising:

(a) a hollow tube formed from a superelastic material and having a proximal portion and a non-perforated distal portion and defining a first lumen therein;

(b) a solid distal segment configured partially within the non-perforated distal portion of the hollow tube to form a second lumen in fluid communication with the first lumen; and (c) a balloon defining a balloon cavity therein affixed to the distal portion of the angioplasty device and in fluid communication with the second lumen.

11. The angioplasty device of claim 10 further comprising a detachable hub connected to the proximal portion of the hollow tube.

12. The angioplasty device of claim 10 further comprising a helical coil spring arranged coaxially about the distal segment.

13. The angioplasty device of claim 10 wherein the superelastic material forming the hollow tube is selected from the group consisting of a nickel-titanium alloy, nickel and its alloys, and titanium and its alloys.

14. The angioplasty device of claim 10 wherein the distal segment comprises a superelastic material or stainless steel.

15. The angioplasty device of claim 10 wherein the distal segment has a longitudinal length, the distal segment being cylindrical along most of its longitudinal length.

16. The angioplasty device of claim 10 wherein the distal segment has a longitudinal length, the distal segment tapering distally along at least part of its longitudinal length.

17. A method for performing a dilatation procedure, using an angioplasty device having a proximal portion and a distal portion, the angioplasty device comprising a hollow tube formed from a superelastic material and having a proximal portion and a distal portion and defining a lumen therein; a distal segment connected to the distal portion of the hollow tube, the distal segment having a longitudinal length and being solid along most of its longitudinal length, with a fluid flow lumen in the distal segment in fluid communication with the hollow tube; and a balloon defining a balloon cavity therein affixed to the distal portion of the angioplasty device and in fluid communication with the fluid flow lumen of the distal segment; the method comprising:

advancing the angioplasty device through a patient's vasculature so the balloon is located at a stenotic lesion;

inflating the balloon to at least partially dilate the stenotic lesion;

deflating the balloon;

advancing the angioplasty device distally so the balloon is located distally of the stenotic lesion;

advancing a balloon dilatation catheter over the device to the stenotic lesion; and further dilating the stenotic lesion via the balloon dilatation catheter.

18. The method of claim 17 further comprising:

removing the balloon dilatation catheter from the angioplasty device;

advancing a stent delivery catheter with a stent contained therein over the angioplasty device;

deploying the stent from the stent delivery catheter;

withdrawing the stent delivery catheter from the area of stent deployment;

moving the angioplasty device within the stent so the balloon is located therein; and inflating the balloon to further expand the stent.

19. A method of treating a body lumen with an angioplasty device having a proximal portion and a distal portion, the angioplasty device comprising a hollow tube formed from a superelastic material and having a proximal portion and a distal portion and defining a lumen therein; a distal segment connected to the distal portion of the hollow tube, the distal segment having a longitudinal length and being solid along most of its longitudinal length, with a fluid flow lumen in the distal segment in fluid communication with the hollow tube; and a balloon defining a balloon cavity therein affixed to the distal portion of the angioplasty device and in fluid communication with the fluid flow lumen of the distal segment; the method comprising:

advancing the angioplasty device through a patient's vasculature so the balloon is located at the stenotic lesion;

inflating the balloon to dilate the stenosis;

deflating the balloon;

advancing the angioplasty device distally so the balloon is located distally of the stenotic lesion;

advancing a stent delivery catheter with a stent contained therein over the angioplasty device;

deploying the stent from the stent delivery catheter so it radially expands inside the body lumen;

withdrawing the stent delivery catheter;

moving the angioplasty device within the stent so the balloon is located therein; and inflating the balloon to further expand the stent.

20. A method for performing both an angiographic and angioplasty procedure with an angioplasty device having a proximal portion and a distal portion, the angioplasty device comprising a hollow tube formed from a superelastic material and having a proximal portion and a distal portion and defining a lumen therein; a distal segment connected to the distal portion of the hollow tube, the distal segment having a longitudinal length and being solid along most of its longitudinal length, with a fluid flow lumen in the distal segment in fluid communication with the hollow tube; and a balloon defining a balloon cavity therein affixed to the distal portion of the angioplasty device and in fluid communication with the fluid flow lumen of the distal segment; the method comprising:

advancing a diagnostic catheter through a patient's vasculature to a region to be diagnosed and treated;

advancing the angioplasty device through the diagnostic catheter so the balloon is located at the stenotic lesion;

injecting diagnostic fluid through the diagnostic catheter while at least part of the angioplasty device is disposed in the diagnostic catheter to visualize the angioplasty device; and inflating the balloon to dilate the stenotic lesion.

21. A method for performing a dilatation procedure, using an angioplasty device having a proximal portion and a distal portion, the angioplasty device comprising a hollow tube formed from a superelastic material and having a proximal portion and a non-perforated distal portion and defining a first lumen therein; a solid distal segment configured partially within the non-perforated distal portion of the hollow tube to form a second lumen in fluid communication with the first lumen; and a balloon defining a balloon cavity therein affixed to the distal portion of the angioplasty device and in fluid communication with the second lumen; the method comprising:

advancing the angioplasty device through a patient's vasculature so the balloon is located at the stenotic lesion;

inflating the balloon to at least partially dilate the stenotic lesion;

deflating the balloon;

advancing the angioplasty device distally so the balloon is located distally of the stenotic lesion;

advancing a balloon dilatation catheter over the device to the stenotic lesion; and further dilating the stenotic lesion via the balloon dilatation catheter.

22. The method of claim 21 further comprising:

removing the balloon dilatation catheter from the angioplasty device;

advancing a stent delivery catheter with a stent contained therein over the angioplasty device;

deploying the stent from the stent delivery catheter;

withdrawing the stent delivery catheter from the area of stent deployment;

moving the angioplasty device within the stent so the balloon is located therein; and inflating the balloon to further expand the stent.

23. A method of treating a body lumen with an angioplasty device having a proximal portion and a distal portion, the angioplasty device comprising a hollow tube formed from a superelastic material and having a proximal portion and a non-perforated distal portion and defining a first lumen therein; a solid distal segment configured partially within the non-perforated distal portion of the hollow tube to form a second lumen in fluid communication with the first lumen; and a balloon defining a balloon cavity therein affixed to the distal portion of the angioplasty device and in fluid communication with the second lumen; the method comprising:

advancing an angioplasty device through a patient's vasculature so the balloon is located at the stenotic lesion;

inflating the balloon to dilate the stenosis;

deflating the balloon;

advancing the angioplasty device distally so the balloon is located distally of the stenotic lesion;

advancing a stent delivery catheter with a stent contained therein over the angioplasty device;

deploying the stent from the stent delivery catheter so it radially expands inside the body lumen;

withdrawing the stent delivery catheter;

moving the angioplasty device within the stent so the balloon is located therein; and inflating the balloon to further expand the stent.

24. A method for performing both an angiographic and angioplasty procedure with an angioplasty device having a proximal portion and a distal portion, the angioplasty device comprising a hollow tube formed from a superelastic material and having a proximal portion and a non-perforated distal portion and defining a first lumen therein; a solid distal segment configured partially within the non-perforated distal portion of the hollow tube to form a second lumen in fluid communication with the first lumen; and a balloon defining a balloon cavity therein affixed to the distal portion of the angioplasty device and in fluid communication with the second lumen; the method comprising:

advancing a diagnostic catheter through a patient's vasculature to a region to be diagnosed and treated;

advancing the angioplasty device through the diagnostic catheter so the balloon is located at the stenotic lesion;

injecting diagnostic fluid through the diagnostic catheter while at least part of the angioplasty device is disposed in the diagnostic catheter to visualize the angioplasty device; and inflating the balloon to dilate the stenotic lesion.

\* \* \* \* \*